(12) United States Patent
Ward et al.

(10) Patent No.: US 10,457,974 B2
(45) Date of Patent: Oct. 29, 2019

(54) METHODS FOR DIAGNOSING INFECTIOUS DISEASES USING ADSORPTION MEDIA

(71) Applicant: ExThera Medical Corporation, Martinez, CA (US)

(72) Inventors: Robert S. Ward, Lafayette, CA (US); Keith R. McCrea, Concord, CA (US)

(73) Assignee: ExThera Medical Corporation, Martinez, CA (US)

( * ) Notice: Subject to any disclaimer, the term of this patent is extended or adjusted under 35 U.S.C. 154(b) by 0 days.

(21) Appl. No.: 15/341,416

(22) Filed: Nov. 2, 2016

(65) Prior Publication Data

US 2017/0073727 A1 Mar. 16, 2017

Related U.S. Application Data

(63) Continuation-in-part of application No. 14/885,729, filed on Oct. 16, 2015, which is a continuation-in-part
(Continued)

(51) Int. Cl.
*C12Q 1/24* (2006.01)
*C12Q 1/70* (2006.01)
(Continued)

(52) U.S. Cl.
CPC ........... *C12Q 1/24* (2013.01); *B01D 15/3828* (2013.01); *C12Q 1/689* (2013.01); *C12Q 1/701* (2013.01);
(Continued)

(58) Field of Classification Search
CPC ............ A61M 1/36; A61M 1/34; B01D 39/04; B01D 39/08; B01D 39/16; B01D 63/08;
(Continued)

(56) References Cited

U.S. PATENT DOCUMENTS

| | | | |
|---|---|---|---|
| 4,103,685 A | 8/1978 | Lupien et al. | |
| 4,415,665 A | 11/1983 | Mosbach et al. | |

(Continued)

FOREIGN PATENT DOCUMENTS

| | | |
|---|---|---|
| CN | 101370536 A | 2/2009 |
| CN | 102740859 A | 10/2012 |

(Continued)

OTHER PUBLICATIONS

Celik et al., ( J. of Clinical Apheresis. vol. 31, Issue 5. Oct. 2016. First published Sep. 10, 2015. pp. 476-478.).*
(Continued)

*Primary Examiner* — Jana A Hines
(74) *Attorney, Agent, or Firm* — Kilpatrick Townsend & Stockton LLP

(57) ABSTRACT

The present invention provides an in vitro method for concentrating infectious pathogens found in a biological sample obtained from an individual who is suspected of being infected with the pathogens. Provided herein is also an in vitro method for reducing or eliminating blood cells from a sample obtained from an individual suspected to being infected with an infectious pathogen. The present invention also provides a method for diagnosing malaria and a method for determining if an individual is infected with a pathogen. Provided herein is also a concentrator and a kit for use with the methods.

11 Claims, 1 Drawing Sheet

Related U.S. Application Data of application No. PCT/US2014/064419, filed on Nov. 6, 2014.

(60) Provisional application No. 61/902,070, filed on Nov. 8, 2013.

(51) Int. Cl.
  *C12Q 1/689* (2018.01)
  *B01D 15/38* (2006.01)

(52) U.S. Cl.
  CPC ....... *C12Q 1/707* (2013.01); *C12Q 2600/158* (2013.01); *G01N 2333/195* (2013.01); *G01N 2333/43556* (2013.01); *G01N 2333/445* (2013.01)

(58) Field of Classification Search
  CPC ........ B01D 63/10; B01D 65/08; B01D 71/08; B01D 15/3828; C07H 1/00; C12M 1/00; C12Q 1/24; C12Q 1/70; C12Q 1/701; C12Q 1/707; C12Q 2600/158; G01N 33/56905; G01N 2333/195; G01N 2333/43556; G01N 2333/445; G01N 2469/10; Y02A 50/60; Y02A 50/57; Y02A 50/58
  USPC .......... 435/5, 6.12, 7.92, 34, 287.2; 422/527
  See application file for complete search history.

(56) References Cited

U.S. PATENT DOCUMENTS

| | | | |
|---|---|---|---|
| 4,430,496 A | 2/1984 | Abbott | |
| 4,613,665 A | 9/1986 | Larm | |
| 4,637,994 A | 1/1987 | Tani et al. | |
| 4,820,302 A | 4/1989 | Woodroof | |
| 4,955,870 A | 9/1990 | Ridderheim et al. | |
| 5,116,962 A | 5/1992 | Stueber et al. | |
| 5,211,850 A | 5/1993 | Shettigar et al. | |
| 5,403,917 A | 4/1995 | Boos et al. | |
| 5,437,861 A | 8/1995 | Okarma et al. | |
| 5,447,859 A | 9/1995 | Prussak | |
| 5,476,509 A | 12/1995 | Keogh, Jr. et al. | |
| 5,753,227 A | 5/1998 | Strahilevitz | |
| 6,037,458 A | 3/2000 | Hirai et al. | |
| 6,159,377 A | 12/2000 | Davankov et al. | |
| 6,197,568 B1 | 3/2001 | Marks et al. | |
| 6,248,127 B1 | 6/2001 | Shah et al. | |
| 6,312,907 B1 | 11/2001 | Guo et al. | |
| 6,461,665 B1 | 10/2002 | Scholander | |
| 6,544,727 B1 | 4/2003 | Hei | |
| 6,559,290 B1 | 5/2003 | Nakatani et al. | |
| 6,653,457 B1 | 11/2003 | Larm et al. | |
| 7,179,660 B1 | 2/2007 | Kirakossian | |
| 7,408,045 B2 | 8/2008 | Maruyama et al. | |
| 7,695,609 B2 | 4/2010 | Soundarrajan et al. | |
| 8,663,148 B2 | 3/2014 | Larm et al. | |
| 8,758,286 B2 | 6/2014 | Ward et al. | |
| 9,173,989 B2 | 11/2015 | Larm et al. | |
| 9,408,962 B2 | 8/2016 | Ward et al. | |
| 9,669,150 B2 | 6/2017 | Larm et al. | |
| 9,764,077 B2 | 9/2017 | Larm et al. | |
| 10,086,126 B2 | 10/2018 | Ward et al. | |
| 10,188,783 B2 | 1/2019 | Larm et al. | |
| 2001/0005487 A1 | 6/2001 | Kamibayashi et al. | |
| 2002/0018985 A1 | 2/2002 | Eibl et al. | |
| 2002/0058032 A1 | 5/2002 | Hirai et al. | |
| 2002/0068183 A1 | 6/2002 | Huang et al. | |
| 2002/0197249 A1 | 12/2002 | Brady et al. | |
| 2002/0197252 A1 | 12/2002 | Brady et al. | |
| 2003/0021780 A1 | 1/2003 | Smith et al. | |
| 2003/0044769 A1 | 3/2003 | Ogino et al. | |
| 2003/0148017 A1 | 8/2003 | Tuominen et al. | |
| 2004/0084358 A1 | 5/2004 | O'Mahony et al. | |
| 2004/0115278 A1 | 6/2004 | Putz et al. | |
| 2004/0140265 A1 | 7/2004 | Lihme | |
| 2004/0176672 A1 | 9/2004 | Silver et al. | |
| 2004/0182783 A1 | 9/2004 | Walker et al. | |
| 2004/0185553 A9 | 9/2004 | Hei | |
| 2004/0202783 A1 | 10/2004 | Baumann et al. | |
| 2005/0098500 A1 | 5/2005 | Collins et al. | |
| 2005/0142542 A1 | 6/2005 | Hei et al. | |
| 2005/0244371 A1 | 11/2005 | Lentz | |
| 2005/0271653 A1 | 12/2005 | Strahilevitz | |
| 2006/0093999 A1 | 5/2006 | Hei | |
| 2006/0252054 A1 | 11/2006 | Ping | |
| 2007/0190050 A1 | 8/2007 | Davidner et al. | |
| 2007/0218514 A1 | 9/2007 | Smith et al. | |
| 2007/0231217 A1 | 10/2007 | Clintone et al. | |
| 2008/0021365 A1 | 1/2008 | Kobayashi et al. | |
| 2008/0138434 A1 | 6/2008 | Brady et al. | |
| 2008/0268464 A1 | 10/2008 | Schumacher et al. | |
| 2008/0314817 A1 | 12/2008 | Fujita et al. | |
| 2009/0105194 A1 | 4/2009 | Flengsrud et al. | |
| 2009/0136586 A1 | 5/2009 | Larm et al. | |
| 2009/0206038 A1 | 8/2009 | Thomas | |
| 2009/0246800 A1 | 10/2009 | Mattingly et al. | |
| 2009/0325276 A1* | 12/2009 | Battrell | B01F 11/0071 435/287.2 |
| 2010/0069816 A1 | 3/2010 | Brady et al. | |
| 2010/0079360 A1 | 4/2010 | McLaughlin et al. | |
| 2010/0098666 A1 | 4/2010 | Wright | |
| 2010/0112725 A1 | 5/2010 | Babu et al. | |
| 2010/0145317 A1 | 6/2010 | Laster et al. | |
| 2010/0216226 A1 | 8/2010 | Hyde et al. | |
| 2010/0217173 A1 | 8/2010 | Hyde et al. | |
| 2010/0239673 A1 | 9/2010 | Linhardt | |
| 2010/0249689 A1 | 9/2010 | Larm et al. | |
| 2010/0276359 A1 | 11/2010 | Ippommatsu et al. | |
| 2010/0291588 A1 | 11/2010 | McDevitt | |
| 2010/0326916 A1 | 12/2010 | Wrazel et al. | |
| 2011/0150911 A1 | 6/2011 | Choo | |
| 2011/0171713 A1 | 7/2011 | Bluchel et al. | |
| 2011/0184377 A1* | 7/2011 | Ward | A61K 31/60 604/500 |
| 2011/0224645 A1 | 9/2011 | Winqvist et al. | |
| 2012/0040429 A1 | 2/2012 | Federspiel et al. | |
| 2012/0305482 A1 | 12/2012 | McCrea et al. | |
| 2013/0102948 A1 | 4/2013 | Reich et al. | |
| 2013/0131423 A1 | 5/2013 | Wang et al. | |
| 2014/0012097 A1 | 1/2014 | McCrea et al. | |
| 2014/0131276 A1 | 5/2014 | Larm et al. | |
| 2014/0231357 A1 | 8/2014 | Ward et al. | |
| 2015/0111849 A1 | 4/2015 | McCrea et al. | |
| 2015/0260715 A1 | 9/2015 | Hu et al. | |
| 2016/0022898 A1 | 1/2016 | Larm et al. | |
| 2016/0082177 A1 | 3/2016 | Ward et al. | |
| 2016/0084835 A1 | 3/2016 | Ward et al. | |
| 2016/0101229 A1 | 4/2016 | McCrea et al. | |
| 2016/0214935 A1 | 7/2016 | Hutchinson et al. | |
| 2016/0331886 A1 | 11/2016 | Ward et al. | |
| 2017/0035956 A1 | 2/2017 | McCrea et al. | |
| 2017/0340803 A1 | 11/2017 | Larm et al. | |
| 2018/0361050 A1 | 12/2018 | Ward et al. | |
| 2019/0038826 A1 | 2/2019 | McCrea et al. | |
| 2019/0143027 A1 | 5/2019 | Larm et al. | |

FOREIGN PATENT DOCUMENTS

| | | |
|---|---|---|
| DE | 4217917 A1 | 12/1993 |
| EP | 0 306 617 A | 3/1989 |
| EP | 0 321 703 A | 6/1989 |
| EP | 0533946 A1 | 3/1993 |
| EP | 0 616 845 A | 9/1994 |
| EP | 0 810 027 A | 12/1997 |
| EP | 1044696 A2 | 10/2000 |
| EP | 1 057 529 A | 12/2000 |
| EP | 1 110 602 A | 6/2001 |
| EP | 1 219 639 A | 7/2002 |
| EP | 2087916 A1 | 8/2009 |
| EP | 2556849 A1 | 2/2013 |
| GB | 2 172 812 A | 10/1986 |
| JP | 58-053757 A | 3/1983 |

(56) References Cited

FOREIGN PATENT DOCUMENTS

| | | | | |
|---|---|---|---|---|
| JP | 4-89500 A | 3/1992 | | |
| JP | 6040926 A | 2/1994 | | |
| JP | 6-505248 A | 6/1994 | | |
| JP | 7-178161 A | 7/1995 | | |
| JP | 96-510166 A | 10/1996 | | |
| JP | 11-502703 A | 3/1999 | | |
| JP | 2000-086688 A | 3/2000 | | |
| JP | 2000-217575 A | 8/2000 | | |
| JP | 2000-515543 A | 11/2000 | | |
| JP | 2002-505101 A | 2/2002 | | |
| JP | 2003-128502 A | 5/2003 | | |
| JP | 2005-514127 A | 5/2005 | | |
| JP | 2005-532130 A | 10/2005 | | |
| JP | 2009-521413 A | 6/2009 | | |
| JP | 2010-530288 A | 9/2010 | | |
| JP | 2013-512078 A | 4/2013 | | |
| KR | 10-2008-0077405 A | 8/2008 | | |
| WO | 91/04086 A | 4/1991 | | |
| WO | 92/14361 A1 | 9/1992 | | |
| WO | 94/26399 A1 | 11/1994 | | |
| WO | 95/05400 | 2/1995 | | |
| WO | 96/29083 A1 | 9/1996 | | |
| WO | 96/40857 A1 | 12/1996 | | |
| WO | 97/35660 A1 | 10/1997 | | |
| WO | 98/05341 A1 | 2/1998 | | |
| WO | 98/29727 A2 | 7/1998 | | |
| WO | 99/06086 A1 | 2/1999 | | |
| WO | 99/45104 A3 | 11/1999 | | |
| WO | WO 200023792 | * | 4/2000 | ........... G01N 33/569 |
| WO | 00/038763 | 7/2000 | | |
| WO | 00/66260 A | 11/2000 | | |
| WO | 01/18060 A | 3/2001 | | |
| WO | 02/060512 | 8/2002 | | |
| WO | 03/033143 A1 | 4/2003 | | |
| WO | 2003/057356 A2 | 7/2003 | | |
| WO | 2004/008138 A2 | 1/2004 | | |
| WO | 2004/009798 A2 | 1/2004 | | |
| WO | 2005/021799 A2 | 3/2005 | | |
| WO | 2007/058592 A1 | 5/2007 | | |
| WO | 2007/069983 A1 | 6/2007 | | |
| WO | 2007/101064 A2 | 9/2007 | | |
| WO | 2007/146162 A2 | 12/2007 | | |
| WO | 2008/095905 A2 | 8/2008 | | |
| WO | 2008/157570 A2 | 12/2008 | | |
| WO | 2010/029317 A2 | 3/2010 | | |
| WO | 2011/068897 A1 | 6/2011 | | |
| WO | 2011/100354 A1 | 8/2011 | | |
| WO | 2012/112724 A1 | 8/2012 | | |
| WO | 2012/172341 A2 | 12/2012 | | |
| WO | WO 2015069942 | * | 11/2013 | ............... C12Q 1/24 |
| WO | 2013/188073 A1 | 12/2013 | | |
| WO | 2014/209782 A1 | 12/2014 | | |
| WO | 2015/069942 A1 | 5/2015 | | |
| WO | WO 2015164198 | * | 10/2015 | ............... A16M 1/36 |

OTHER PUBLICATIONS

Klinghardt. (Therapeutic Apheresis in the Treatment of Lyme Disease. http://www.klinghardtacademy.com/images/stories/Lyme_Disease/Therapeutic_Apheresis_in_the_Treatment_of_Lyme_Disease_8-2013.pdf) (Year: 2013).*
Klinghardt (Therapeutic Apheresis in the Treatment of Lyme Disease) presented at the Lyme Recovery 2013 Online Conference Dated Saturday May 4, 2013—8:30am to 6:00pm PST. The associated webpage was created on May 7, 2013 and Last updated on Oct. 1, 2013. (Year: 2013).*
Francy, D. et al., "Comparison of filters for concentrating microbial indicators and pathogens in lake water samples," Applied and Environmental Microbiology, 79(4):1342-52, 2012.
Millen, H. et al., "Glass wool filters for concentrating waterborne viruses and agricultural zoonotic pathogens," J. Vis. Exp., 61:e3930, 2012.
Abdul-Razzak, K. et al., "Fetal and newborn calf thymus as a source of chromatin proteins: Purification of HMG-1 and HMG-2," Preparative Biochemistry and Biotechnology, 17(1):51-61, 1987.
Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.
Bhakdi, S. and Tranum-Jensen, J., "Alpha-toxin of *Staphylococcus aureus*," Microbiological Reviews, 55(4):733-751, 1991.
Bindslev. L. et al., "Treatment of acute respiratory failure by extracorporeal carbon dioxide elimination performed with a surface heparinized artificial lung," Anesthesiology, 67(1):117-120, 1987.
Bjorklund, M. et al., Abstract of "Synthesis of silica-based heparin-affinity adsorbents," J. Chrom. A., 728(1-2):149-169, 1996.
Chase, H., "Affinity separations utilising immobilised monoclonal antibodies—a new tool for the biochemical engineer," Chemical Engineering Science, 39(7-8):1099-1125, 1984.
Chen, Y. et al., "Microbial subversion of heparin sulfate proteoglycans," Mol. Cells, 26:415-426, 2008.
Dixon, T. et al., "Anthrax," New England Journal of Medicine, 341(11):815-826, 1999.
Dubreuil, J. et al., "Effect of heparin binding on Helicobacter pylori resistance to serum," J. Med. Micro., 53:9-12, 2004.
Fujita, M. et al., "Adsorption of inflammatory cytokines using a heparin-coated extracorporeal circuit," Artificial Organs, 26(12):1020-1025, 2002.
Garg, L. et al., "Isolation and separation of HMG proteins and histones H1 and H5 and core histones by column chromatography on phosphocellulose," Protein Expression and Purification, 14(2):155-159, 1998.
Haase, M. et al., "The effect of three different miniaturized blood purification devices on plasma cytokine concentration in an ex vivo model of endotoxinemia," Int. J. Artif. Organs, 31(8):722-729, 2008.
Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.
International Preliminary Report on Patentability, dated Aug. 21, 2013, PCT Application No. PCT/US2012/025316; 8 pages.
International Search Report; PCT/US2012/025316 dated May 23, 2012.
International Search Report; PCT/US2010/058596 dated Mar. 29, 2011.
International Search Report; PCT/US2011/024229 dated May 30, 2011.
International Search Report; PCT/SE2006/001421 dated Mar. 30, 2007.
International Search Report; PCT/US2013/042377 dated Sep. 9, 2013.
International Search Report; PCT/US2014/043358 dated Dec. 1, 2014.
International Search Report; PCT/US2014/064419 dated Feb. 12, 2015.
International Search Report; PCT/US2015/026340 dated Jul. 28, 2015.
International Search Report; PCT/US2015/051239 dated Dec. 17, 2015.
International Search Report; PCT/US2016/057121 dated Dec. 30, 2016.
Kadam, P. et al., "Jarisch-Herxheimer Reaction in a Patient with Disseminated Lyme Disease," Journal of Case Reports, 3(2):362-365, 2013.
Keuren, J. et al., "Thrombogenecity of polysaccharide-coated surfaces," Biomaterials, 24:1917-24, 2003.
Kim et al., "Role of the heparin in regulating a transcapillary exchange in far north conditions," Bulletin of the Siberian Branch of the Russian Academy of Medical Sciences, 2(108), 2003.
Larm, O. et al., "A new non-thrombogenic surface prepared by selective covalent binding of heparin via a modified reducing terminal residue," Biomater Med Devices Artif Organs, 11(2&3):161-173, 1983.

(56) References Cited

OTHER PUBLICATIONS

Low, R. et al., "Protein n, a primosomal DNA replication protein of *Escherichia coli*," Journal of Biological Chemistry, 257(11):6242-6250, 1982.
Lopatkin et al., "Efferent methods in medicine, M.," Medicine, pp. 266, 272-273, 276-279, 1989.
Mandal, C. and Mandel, C. "Sialic acid binding lectins," Experientia, 46:433-439, 1990.
Mariano, F. et al, "Tailoring high-cut-off membranes and feasible application in sepsis-associated acute renal failure: in vitro studies," Nephrol Dial Transplant, 20:1116-1126, 2005.
Nadkarni, V. et al., Abstract of "Directional immobilization of heparin onto beaded supports," Anal. Biochem., 222(1):59-67, 1994.
Ofek, I. and Beachey, E., "Mannose binding and epithelial cell adherence of *Escherichia coli*," Infection and Immunity, 22(1):247-254, 1978.
Park, P. et al., "Activation of Syndecan-1 ectodomain shedding by *Staphylococcus aureus* α-toxin and β-toxin," J. Biol. Chem., 279(1):251-258, 2004.
Popova, T. et al., "Acceleration of epithelial cell syndecan-1 shedding by anthrax hemolytic virulence factors," BMC Microbiolgy, 6:8, pp. 1-16, 2006.
Rauvala, H. et al., "Isolation and some characteristics of an adhesive factor of brain that enhances neurite outgrowth in central neurons," Journal of Biological Chemistry, 262(34):16625-16635, 1987.
Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.
Riesenfeld, J. and Roden, L., "Quantitative analysis of N-sulfated, N-acetylated, and unsubstituted glucosamine amino groups in heparin and related polysaccharides," Anal Biochem, 188:383-389, 1990.
Sagnella, S. et al., "Chitosan based surfactant polymers designed to improve blood compatibility on biomaterials," Colloids and Surfaces B: Biointerfaces, 42:147-155, 2005.
Salmivirta, M. et al., "Neurite growth-promoting protein (Amphoterin, p30) binds syndecan," Experimental Cell Research, 200:444-451, 1992.
Sanchez, J. et al., "Control of contact activation on end-point immobilized heparin: The role of antithrombin and the specific antithrombin-binding sequence," J. Bio. Mat. Res., 29:665-661, 1995.
Sasaki, H. et al., Abstract: "Improved method for the immobilization of heparin," J. Chrom., 400:123-32, 1987.
Sato, T. et al., "Experimental study of extracorporeal perfusion for septic shock," Asaio Journal, 39(3):M790-M793, 1993.
Schefold, J. et al., "A novel selective extracorporeal intervention in sepsis: immunoadsorption of endotoxin, interleukin 6, and complement-activating product 5A," Shock, 28(4):418-425, 2007.
Sharon, N., "Bacterial lectins, cell-cell recognition and infectious disease," FEBS letters, 217(2):145-157, 1987.
Swartz, M., "Recognition and management of anthrax—an update," New Engl. J. Med., 345(22):1621-1626, 2001.
Thomas, R. and Brooks, T., "Common oligosaccharide moieties inhibit the adherence of typical and atypical respiratory pathogens," Journal of Microbiology, 53:833-840, 2004.
Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.
Wang, H. et al., "HMG-1 as a late mediator of endotoxin lethality in mice," Science, 285:248-251, 1999.
Ward, R. et al., "Specificity of adsorption in a prototype whole blood affinity therapy device for removal of *Staphylococcus aureus*," Society for Biomaterials 2013 Annual Meeting and Exposition, Apr. 10, 2013, p. 1.
Weber, V. et al., "Development of specific adsorbents for human tumor necrosis factor-α: influence of antibody immobilization on performance and biocompatibility," Biomacromolecules, 6:1864•1870, 2005.
Weir, D., "Carbohydrates as recognition molecules in infection and immunity," FEMS Microbiology Immunology, 47:331-340, 1989.
Wendel, H. and Ziemer, G., "Coating-techniques to improve the hemocompatibility of artificial devices used for extracorporeal circulation," European Journal of Cardio-thoracic Surgery, 16:342-350, 1999.
Yu, J. et al., "Adhesion of coagulase-negative staphylococci and adsorption of plasma proteins to heparinized polymer surfaces," Biomaterials, 15(10):805-814, 1994.
Zhou, M. and Reznikoff, W., Abstract: "Heparin-agarose aqueous ethanol suspension," J. Mol. Bio., 271(3):12, 1997.
Axelsson, J. et al., "Cytokines in blood from septic patients interact with surface-immobilized heparin," ASAIO Journal, 56:48-51, 2010.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Kishimoto, S. et al., "Human stem cell factor (SCF) is a heparin-binding cytokine," J. Biochem., 145(3):275-278, 2009.
Salek-Ardakani, S. et al., "Heparin and heparan sulfate bind interleukin-10 and modulate its activity," Blood, 96:1879-1888, 2000.
International Search Report; PCT/US2017/058536; dated Jan. 17, 2018.
Alfaro et al., "Interleukin-8 in cancer pathogenesis, treatment and follow-up," Cancer Treat Rev., Nov. 2017, vol. 60:24-31 (abstract only).
Kumari, N. et al., "Role of interleukin-6 in cancer progression and therapeutic resistance," Tumour Biol., Sep. 2016, vol. 37(9), pp. 11553-11572 (abstract only).
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Mattsby-Baltzer, I. et al., "Affinity apheresis for treatment of bacteremia caused by *Staphylococcus aureus* and/or methicillin-resistant *S. aureus* (MRSA)," J. Microbiol. Biotechnol., 21(6):659-664, 2011.
Waugh D. and Wilson, C., "The interleukin-8 pathway in cancer," Clin. Cancer Res., 14(21):6735-41, 2008.
Webb, L. et al., "Binding to heparan sulfate or heparin enhances neutrophil responses to interleukin 8," PNAS USA, 90:7158-62, 1993.

\* cited by examiner

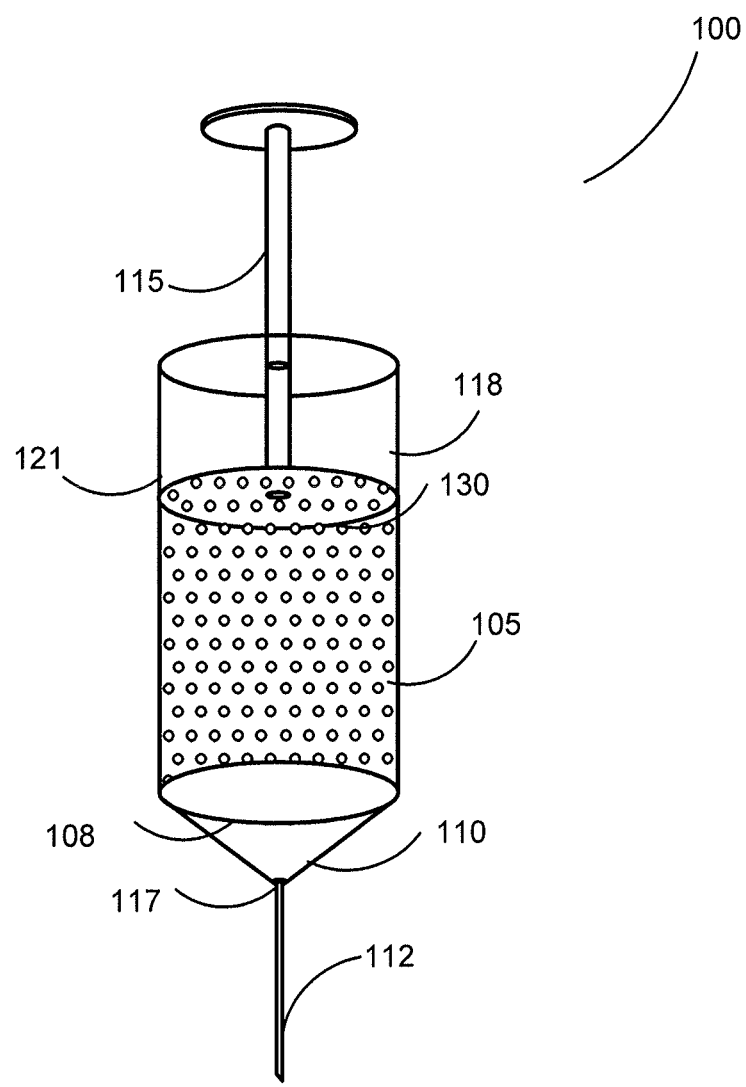

METHODS FOR DIAGNOSING INFECTIOUS DISEASES USING ADSORPTION MEDIA

CROSS-REFERENCE TO RELATED APPLICATIONS

This application is a continuation-in-part of U.S. patent application Ser. No. 14/885,729, filed Oct. 16, 2015 which is a continuation-in-part application of PCT/US2014/064419, filed Nov. 6, 2014, which application claims priority to U.S. Provisional Application No. 61/902,070, filed Nov. 8, 2013, the disclosures of which are hereby incorporated by reference in their entirety for all purposes.

BACKGROUND OF THE INVENTION

Early detection of infectious diseases is necessary to control their spread, to direct therapy, and to improve patient outcomes. For example, early and accurate identification of outbreaks of deadly pathogens can prevent the occurrence of global pandemics. Currently, many diagnostic methods for bloodstream infections caused by, for example, viruses (including Ebola and related filoviruses) or drug-resistant bacteria, require at least 24 hours or longer to perform. There is a need in the art for a method to minimize the time needed to detect the presence of a pathogen in an individual's sample. The goal is to detect the pathogen while it is still present at very low concentrations, if possible, before clinical symptoms are evident. Early intervention may then minimize the intensity and duration of the infection thereby reducing morbidity and mortality.

In some cases, the presence of cells such as blood cells (e.g., red blood cells and white blood cells) in the sample reduces the specificity and sensitivity of the assay method. At present, there exists no means for rapid isolation and collection of an infectious pathogen from a biological sample such that the pathogen can be identified or analyzed when present at very low concentration. In addition, there is a need in the art for technologies that can improve the sensitivity of existing diagnostic methods for detecting pathogens. The present invention satisfies these and other needs.

BRIEF SUMMARY OF THE INVENTION

In one aspect, the present invention provides an in vitro method for concentrating a wide range of infectious pathogens and toxins present in a biological sample obtained from a subject who is suspected of being infected with said pathogens. The method comprises: (a) contacting the biological sample obtained from the subject with a broad-spectrum adsorption media under conditions that form an adhering complex comprising the adsorption media and said pathogens; (b) separating the adhering complex from components of the sample that are not included in the complex while maintaining the complex, e.g, by washing the adhering complex with a buffer solution; and (c) collecting pathogens of the adhering complex by applying an elution buffer to the complex, thereby concentrating the infectious pathogens in an eluent. In some embodiments, the method further comprises detecting the isolated infectious pathogens. In some instances, detecting the isolated infectious pathogens comprises a colorimetric assay, an immunoassay, an enzyme-linked immunosorbent assay (ELISA), a PCR-based assay, a pathogen growth assay with optional staining, or a combination thereof.

In some embodiments, the wash buffer is a normal saline solution. In some embodiments, the elution buffer is a high ionic strength or hypertonic saline solution.

In some embodiments, the biological sample is selected from the group consisting of whole blood, serum, plasma, urine, feces, sputum, tears, saliva, bronchial lavage fluid, other bodily fluid, and combinations thereof.

In some embodiments, the adsorption media is a solid substrate of high surface area having at least one polysaccharide molecular adsorbent on the surface thereof. In some embodiments, the at least one polysaccharide adsorbent is attached to the surface of the solid substrate by end-point attachment. In some embodiments, the at least one polysaccharide adsorbent is a member selected from the group consisting of heparin, heparan sulfate, mannose, dextran sulfate, hyaluronic acid, salicylic acid, chitosan, and a combination thereof. In some instances, the mannose is D-mannose or a D-mannose polymer. In some instances, the at least one polysaccharide adsorbent is heparin and mannose.

In some embodiments, the solid substrate comprises a plurality of rigid polymer beads. The plurality of rigid polymer beads can be rigid polyethylene beads.

In some embodiments, the pathogens are selected from the group consisting of *Plasmodium falciparum, Plasmodium vivax, Plasmodium ovale, Plasmodium malariae*, Ebola virus (EBOV), non-EBOV Filovirus, Flaviviridae, *Streptococcus aureus, Escherichia coli*, carbapenem-resistant *enterobacteriaceae* (CRE) bacteria, an ESBL-producing pathogen, vancomycin-resistant *enterococci* (VRE) bacteria, *Acinetobacter baumannii, Klebsiella pneumoniae, Klebsiella oxytoca, Enterococcus faecalis, Enterococcus faecium, Candida albicans*, cytomegalovirus (CMV), Adenovirus, herpes simplex virus 1 (HSV1), herpes simplex virus 2 (HSV2), *Borrelia burgdorferi, Borrelia mayonii, Borrelia afzelii, Borrelia garinii*, and any combination thereof.

In a second aspect, the present invention provides an in vitro method for reducing or eliminating blood cells from a biological sample obtained from a subject who is suspected of being infected with a pathogen. The method comprises: (a) contacting the biological sample obtained from the subject with an optionally broad-spectrum adsorption media under conditions to form an adhering complex comprising the adsorption media and a pathogen present in the sample; and (b) separating the blood cells of the sample and the adhering complex while maintaining the adhering complex, thereby reducing or eliminating the blood cells from the sample. In some embodiments, step (b) further comprises washing the adhering complex with a saline solution. In some embodiments, the method further comprises (c) applying an elution buffer to the adhering complex; and (d) collecting the pathogen of the adhering complex. In some embodiments, the method further comprises detecting the isolated infectious pathogens. In some instances, detecting the isolated infectious pathogens comprises a colorimetric assay, an immunoassay, an enzyme-linked immunosorbent assay (ELISA), a PCR-based assay, a pathogen growth assay, or a combination thereof.

In some embodiments, the wash buffer is a saline solution. In some embodiments, the elution buffer is a high ionic or hypertonic saline solution In some embodiments, the biological sample is selected from the group consisting of whole blood, serum, plasma, urine, feces, sputum, tears, saliva, bronchial lavage fluid, other bodily fluid, and combinations thereof.

In some embodiments, the adsorption media is a solid substrate of high surface area having at least one polysaccharide adsorbent on the surface thereof. In some embodiments, the at least one polysaccharide adsorbent is attached to the surface of the solid substrate by end-point attachment. In some embodiments, the at least one polysaccharide adsorbent is a member selected from the group consisting of heparin, heparan sulfate, mannose, dextran sulfate, hyaluronic acid, salicylic acid, chitosan, and a combination thereof. In some instances, the mannose is D-mannose or a D-mannose polymer. In some instances, the at least one polysaccharide adsorbent is heparin and mannose.

In some embodiments, the solid substrate comprises a plurality of rigid polymer beads. The plurality of rigid polymer beads can be rigid polyethylene beads.

In some embodiments, the pathogens are selected from the group consisting of *Plasmodium falciparum, Plasmodium vivax, Plasmodium ovale, Plasmodium malariae*, Ebola virus (EBOV), *Streptococcus aureus, Escherichia coli*, carbapenem-resistant *enterobacteriaceae* (CRE) bacteria, an ESBL-producing pathogen, vancomycin-resistant *enterococci* (VRE) bacteria, *Acinetobacter baumannii, Klebsiella pneumoniae, Klebsiella oxytoca, Enterococcus faecalis, Enterococcus faecium, Candida albicans*, cytomegalovirus (CMV), herpes simplex virus 1 (HSV1), herpes simplex virus 2 (HSV2), *Borrelia burgdorferi, Borrelia mayonii, Borrelia afzelii, Borrelia garinii*, and any combination thereof.

In a third aspect, the present invention provides an in vitro method for diagnosing malaria in a subject who is suspected of being infected with *Plasmodium*. The method comprises (a) contacting a sample obtained from said subject with an adsorption media under conditions to form an adhering complex comprising the adsorption media and a cell present in the sample which is infected with *Plasmodium*; (b) determining the presence of the adhering complex by detecting a physical change to the adsorption media; and (c) predicting that the subject has malaria based on the physical change to the adsorption media compared to a reference adsorption media that has been contacted with a control sample. In some embodiments, the method further comprises generating a standard curve of the physical change to the reference media that has been contacted with the control sample.

In some embodiments, the biological sample is selected from the group consisting of whole blood, serum, plasma, urine, feces, sputum, tears, saliva, bronchial lavage fluid, other bodily fluid, and combinations thereof. In some instances, the sample is whole blood.

In some embodiments, the control sample is a sample from a healthy subject. In some embodiments, the control sample is a sample from a subject with malaria.

In some embodiments, the physical change is the color of the adsorption media.

In some embodiments, the adsorption media is a solid substrate of high surface area having at least one polysaccharide adsorbent on the surface thereof. In some embodiments, the at least one polysaccharide adsorbent is attached to the surface of the solid substrate by end-point attachment. In some embodiments, the at least one polysaccharide adsorbent is a member selected from the group consisting of heparin, heparan sulfate, mannose, dextran sulfate, hyaluronic acid, salicylic acid, chitosan, and a combination thereof. In some instances, the mannose is D-mannose or a D-mannose polymer. In some instances, the at least one polysaccharide adsorbent is heparin and mannose.

In some embodiments, the solid substrate comprises a plurality of rigid polymer beads. The plurality of rigid polymer beads can be rigid polyethylene beads.

In a third aspect, the present invention provides an in vitro method for determining that a subject is infected with an infectious pathogen. The method comprises (a) contacting a whole blood sample obtained from said subject with an adsorption media to form an adhering complex comprising the adsorption media and a pathogen present in the sample; (b) determining presence of the adhering complex by detecting a physical change to the adsorption media; and (c) predicting that the subject is infected by the infectious pathogen based on the physical change to the adsorption media compared to a reference adsorption media that has been contacted with a control sample. In some embodiments, the method further comprises generating a standard curve of the physical change to the reference media that has been contacted with the control sample.

In some embodiments, the biological sample is selected from the group consisting of whole blood, serum, plasma, urine, feces, sputum, tears, saliva, bronchial lavage fluid, other bodily fluid, and combinations thereof. In some instances, the sample is whole blood.

In some embodiments, the control sample is a sample from a healthy subject. In some embodiments, the control sample is a sample from a subject infected with the infectious pathogen.

In some embodiments, the physical change is the color of the adsorption media.

In some embodiments, the adsorption media is a solid substrate of high surface area having at least one polysaccharide adsorbent on the surface thereof. In some embodiments, the at least one polysaccharide adsorbent is attached to the surface of the solid substrate by end-point attachment. In some embodiments, the at least one polysaccharide adsorbent is a member selected from the group consisting of heparin, heparan sulfate, mannose, dextran sulfate, hyaluronic acid, salicylic acid, chitosan, and a combination thereof. In some instances, the mannose is D-mannose or a D-mannose polymer. In some instances, the at least one polysaccharide adsorbent is heparin and mannose.

In some embodiments, the solid substrate comprises a plurality of rigid polymer beads. The plurality of rigid polymer beads can be rigid polyethylene beads.

In some embodiments, the pathogens are selected from the group consisting of *Plasmodium falciparum, Plasmodium vivax, Plasmodium ovale, Plasmodium malariae*, Ebola virus (EBOV), *Streptococcus aureus, Escherichia coli*, carbapenem-resistant *enterobacteriaceae* (CRE) bacteria, an ESBL-producing pathogen, vancomycin-resistant *enterococci* (VRE) bacteria, *Acinetobacter baumannii, Klebsiella pneumoniae, Klebsiella oxytoca, Enterococcus faecalis, Enterococcus faecium, Candida albicans*, cytomegalovirus (CMV), herpes simplex virus 1 (HSV1), herpes simplex virus 2 (HSV2), *Borrelia burgdorferi, Borrelia mayonii, Borrelia afzelii, Borrelia garinii*, and any combination thereof.

In another aspect, the present invention provides an in vitro method for detecting an infectious pathogen present in a biological sample obtained from a subject who is suspected of being infected, the method comprising: (a) contacting the biological sample obtained from the subject with an adsorption media under conditions to form an adhering complex comprising the adsorption media and said pathogen; (b) separating the adhering complex from components of the biological sample that are not included in the complex while maintaining the complex; and (c) collecting the pathogen of the adhering complex, wherein the pathogen or a component of the pathogen is collected after using an enzymatic digestion while the pathogen is resident on the adsorption media.

In some embodiments, the digestion is with one or more enzymes such as a protease or DNase while the pathogen (e.g. virus) is still adsorbed to the media.

These and other aspects, objects and embodiments will become more apparent when read with the detailed description which follows.

BRIEF DESCRIPTION OF THE DRAWING

The FIGURE shows an embodiment of a concentrator of the present invention.

DETAILED DESCRIPTION OF THE INVENTION

The present invention provides methods for infectious disease detection and diagnosis. Advantagously, the present invention can be used to isolate bacteria, viruses, cytokines and other pathogens (e.g., parasites) from a patient sample which can be used in the early detection of an infection. In another aspect of the present invention, cells and other non-analytes that can interfere with analyte detection assay can be removed from the sample using the adsorption media described herein.

Also provided herein are simple chromogenic assay methods for detecting circulating pRBCs and *Plasmodium* from a sample taken from a human subject. The method also can be used to monitor malaria progression during the initiation and/or the completion of the anti-malaria therapy.

It has been surprisingly discovered that parasitemia in pRBCs can be detected by contacting the infected blood with a polysaccharide (e.g., heparin, or heparan sulfate) that has been covalently bound to an adsorption media. The parasites and pRBCs become bound onto the adsorption media, and in turn alter the color of the media. Thus, a visible color change indicates that the subject has a malaria infection.

I. Definitions

As used herein, the following terms have the meanings ascribed to them unless specified otherwise.

The term "malaria infection" refers to an infection caused by the parasitic protozoans of the genus *Plasmodium*, such as, but not limited to, *P. falciparum, P. vivax, P. ovale, P. malariae*, and *P. knowlesi*.

The term "adsorption media" refers to a material to which a cell, polypeptide, polynucleotide, chemical molecule, biological molecule can adhere to the surface thereof.

The term "adhering complex" refers to a complex of at least two molecules wherein the first molecule is attached (e.g., linked, coupled or bound) to the surface of a substrate and the second molecule is attached to the first molecule.

The term "color change" refers to a change from a first color to a second color. If there is no detectable difference in the first color and the second color, then a color change is not indicated.

The term "visible spectrum" refers to the portion of the electromagnetic spectrum, e.g., about 390 to 7000 nm that can be detected by the human eye. Light in the near infrared, medium wavelength infrared, and far wavelength spectrums are not visible by the human eye.

The term "healthy control" refers to an individual who does not have an infection. The term "positive control" refers to an individual with an infection caused by the pathogen of interest.

The term "high surface area" refers to the property of having a large specific surface area to volume ratio.

The term "adsorbent" refers to a solid substrate with a chemical compound, a biological molecule, or a material that is attached (e.g., linked, coupled or bound) thereto. In certain instances, the adsorbent is the solid substrate itself. In one embodiment, an adsorbent is a polymer resin with a polysaccharide bound thereto.

The term "rigid polymer bead" refers to a bead, granule, pellet, sphere, particle, microcapsule, sphere, microsphere, nanosphere, microbead, nanobead, microparticle, nanoparticle, and the like that is made from a polymer resin.

The term "carbohydrate" refers to a molecule containing carbon, hydrogen and oxygen atoms, and usually with the empirical formula $C_x(H_2O)_y$, where x and y are different numbers. Examples of carbohydrates includes monosaccharides, disaccharides, oligosaccharides, and polysaccharides.

The term "polysaccharide" refers to a molecule comprising many monosaccharide units joined together by glycosidic bonds, and having an empirical formula of $C_x(H_2O)_y$, where x is between 200 to about 3000.

The term "anti-malaria therapy" refers to a treatment such as a pharmaceutically effective agent intended to relieve or remedy a malarial infection.

II. Detailed Description of Embodiments

A. Adsorption Media

The adsorption media of the present invention provides a surface to attach a polysaccharide adsorbent that can bind to analytes/pathogens and pRBCs. In some embodiments, the adsorption media includes a solid substrate with a high surface area having at least one polysaccharide adsorbent on the surface thereof. The solid substrate can be made of, for example, but not limited to, polyethylene, polystyrene, polypropylene, polysulfone, polyacrylonitrile, polycarbonate, polyurethane, silica, latex, glass, cellulose, cellulose acetate, crosslinked dextran, crosslinked agarose, chitin, chitosan, crosslinked dextran, crosslinked alginate, silicone, Teflon®, fluoropolymer, and other synthetic polymers. The solid substrate with a high surface area can be a plurality of adsorbent monolayers, filters, membranes, solid fibers, hollow fibers, particles, or beads. Optionally, the solid substrate can be present in other forms or shapes or configured articles providing a large surface area, sufficient to bind a detectable quantity of analyte. The substrate can be configured into different shapes.

Useful substrates for creating the media include, but are not limited to, non-porous rigid beads, particles, or packing, reticulated foams, a rigid monolithic bed (e.g. formed from sintered beads or particles), a column packed with woven or nonwoven fabric, a column packed with a yarn or solid or hollow dense (not microporous) monofilament fibers, a flat film or barrier membrane, a spiral wound cartridge formed from flat film or dense membrane, or a combination of media such as a mixed bead/fabric cartridge.

In certain instances, a suitable substrate is one that is initially microporous, but becomes essentially nonporous when the surface is treated before, during or after the creation of adsorption sites, e.g., via end-point-attached one or more polysaccharide adsorbents. In one embodiment, the substrate is in the form of solid beads or particles.

In certain instances, the solid substrate is a plurality of rigid polymer beads such as polyethylene, polystyrene, polypropylene, polysulfone, polyacrylonitrile, polycarbonate, polyurethane, silica, latex, glass, cellulose, crosslinked agarose, chitin, chitosan, crosslinked dextran, crosslinked alginate, silicone, fluoropolymer, and synthetic polymer beads. Preferably, the rigid polymer beads are polyethylene beads.

In certain aspects, the adsorbtion media (e.g. beads) can be affixed or shaped into a dip stick, a strip, a polymer stick, magnetic beads, or other forms. In fact, the substrate can be configured into different shapes and sizes. The adsorption media can be affixed to or configured into a dip stick or dip strip. For example, a polymer dip stick is suitable for use in the present invention such as one made of rough or sintered ultra high molecular weigh polyethylene (UHMWPE) particles, or other polymers that do not leach or interfere with detection assays. Other substrates or surfaces include metallic, cellulosic, e.g. paper, open-cell foam, magnetic, fibers, and the like, wherein the adsorption media is affixed or coated to these materials. As long as the surface material or substrate for the adsorption media does not release interfering substances, it is suitable for use in the present invention. High-surface areas are preferred for maximizing capture of the analyte.

The size of the solid substrate can be selected according to the volume of the test sample used in the assay or other parameters. In some embodiments, the plurality of rigid polymer beads has an average outer diameter of about 1 µm to about 1 mm, e.g., 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 45 µm, 55 µm, 60 µm, 65 µm, 70 µm, 75 µm, 80 µm, 85 µm, 90 µm, 95 µm, 100 µm, 200 µm, 300 µm, 400 µm, 500 µm, 600 µm, 700 µm, 800 µm, 900 µm, and 1 mm. In other embodiments, the plurality of rigid polymer beads has an average diameter of about 10 µm to about 200 µm, e.g., 10 µm, 15 µm, 20 µm, 25 µm, 30 µm, 35 µm, 45 µm, 55 µm, 60 µm, 65 µm, 70 µm, 75 µm, 80 µm, 85 µm, 90 µm, 95 µm, 100 µm, 105 µm, 110 µm, 115 µm, 120 µm, 125 µm, 130 µm, 135 µm, 140 µm, 145 µm, 150 µm, 155 µm, 160 µm, 165 µm, 170 µm, 175 µm, 180 µm, 185 µm, 190 µm 195 µm, and 200 µm. Useful beads have a size ranging from about 100 to above 500 microns in diameter such as 100, 200, 300, 400, or 500 microns. The average size of the beads can be from 150 to 450 microns. See, for example, WO 2011/068897, the entire contents of which are hereby incorporated by reference.

The surface of the solid substrate can be functionalized to allow the covalent attachment of the polysaccharide adsorbent described herein. In some embodiments, the surface of the solid substrate has at least one chemical group, such as an amine group.

The adsorption media can be conatained within a housing, such as a syringe, a column, cartridge, tube, centrifuge tube, and the like, or any vessel. In some embodiments, the vessel is a particular shape and size such that RBCs that are not captured onto polysaccharide bound adsorption media can be removed without disturbing the parasitized RBCs attached to the media.

The housing comprising the adsorption media can contain more than one type of adsorption media. In some embodiments, the different media is layered in a parfait-type arrangement within the housing such that the sample, e.g., whole blood, contacts the different media in series or parallel flow. One arrangement of the different media within a cartridge is to position a first adsorption media at the entrance and/or the exit of the cartridge, with an optionally blended region containing the second adsorption media interposed between the entrance and exit regions. In the case of media in fiber form, a mixed woven, knitted, or non-woven structure can be prepared by methods well known in the textile industry to form fabric from the mixed fiber. Alternatively, a yarn can be prepared from finer multifilament yarn or monofilament made from two or more fibers with different surface chemistries, as long as one fiber type contains a surface that actively prevents blood clotting on contact. The mixed-fiber yarn can then be used to prepare fabric for blood contact.

B. Polysaccharide Adsorbents

In some embodiments, the polysaccharide adsorbent is heparin, heparan sulfate, mannose, dextran sulfate, hyaluronic acid, sialic acid, chitosan, and a combination thereof. In some instances, one or more different polysaccharide adsorbents, e.g., 1, 2, 3, 4, 5 or more different polysaccharide adsorbents, are attached to the solid substrate of the adsorption media. In some embodiments, the absorbent is heparin. In some embodiments, the absorbent is heparan sulfate. In other embodiments, the absorbent is mannose. In another embodiment, the absorbent is dextran sulfate. In some instances, the polysaccharide adsorbents are heparin and mannose. In some instances, the polysaccharide adsorbents are heparan sulfate and mannose. In other instances, the polysaccharide adsorbents are heparin and dextran sulfate. In yet other instances, the polysaccharide adsorbents are mannose and dextran sulfate.

In some embodiments, more than 1 adsorbent, e.g., 2 absorbents, are attached onto a single solid substrate. In some instances, the ratio of the two adsorbents (A and B) are in the range of 1:99 to 99:1. In other embodiments, the substrate is coated with about 1-50% of adsorbent A and about 1-50% of adsorbent B.

In some embodiments, mannose used as an adsorbent is a reducing sugar or is a non-reducing sugar (e.g., a mannoside). Suitable mannoses include, but are not limited to, D-mannose, L-mannose, p-aminophenyl-α-D-mannopyranoside, a mannose containing polysaccharide, and mannan. The term "mannose" also includes a polymer of mannose such as mannan. Mannan refers to a plant polysaccharide that is a linear polymer of the sugar mannose. Plant mannans have β(1-4) linkages. Mannan can also refer to a cell wall polysaccharide found in yeasts. This type of mannan has a α(1-6) linked backbone and α(1-2) and α(1-3) linked branches.

In one embodiment, the mannose is bound by end-point attachment to the solid substrate. In another embodiment, the mannose is attached to the substrate by multi-point attachment.

In other instances, mannose is a polymer of mannose such as mannan. Mannan refers to a plant polysaccharide that is a linear polymer of the sugar mannose. Plant mannans have β(1-4) linkages. Mannan can also refer to a cell wall polysaccharide found in yeasts. This type of mannan has a α(1-6) linked backbone and α(1-2) and α(1-3) linked branches.

Red blood cells infected by *P. falciparum* express erythrocyte membrane protein 1 (PfEMP1) which can bind to specific binding molecules present on the surface of endothelial cells and other RBCs. The method provided herein is based in part on the ability of parasitized red blood cells to bind select binding molecules, such as polysaccharides. Moreover, when these binding molecules are bound to the surface of an adsorption media, the media can be used to separate pRBCs from a patient sample, which in turn alters the color of the adsorption media. Thus, the presence of a malaria infection can be determined by contacting a patient sample with a binding molecule bound to an adsoprtion media.

Molecules that can bind pRBCs and in particular PfEMP1 include, but are not limited to, polysaccharides, such as glycoaminoglycans, e.g., heparin, heparan sulfate, and chondroitin sulfate A (CSA), siailic acid, the complement receptor 1 (CR1), the ABO blood group antigens A and B, ICAM-1, CD36, trombospondin (TSP), endothelial protein C receptor (EPCR), E-selectin, vascular cell adhesion molecule 1 (VCAM-1), platelet endothelial cell adhesion molecule 1 (PECAM-1), endothelial leukocyte adhersion molecule 1 (ELAM-1), serum proteins IgG/IgM, and fibrinogen, carbohydrates with mannose groups, lectins, and chitosans. Additional pRBC binding molecules include hyluronate, peptidoglycans, glycoproteins, glycolipids, glycans, glycosylphosphatidylinositol (GPI) glycans, and hyaluronic acid, and other neuraminic acids.

The binding molecules provided above can be used to adsorb pRBCs onto a surface. In some embodiments, at least one polysaccharide adsorbent is attached to a solid substrate of high surface area to form an adsorption media. In some embodiments, the polysaccharide adsorbent is heparin, heparan sulfate, hyaluronic acid, sialic acid, carbohydrates with mannose sequences, and chitosan. In one embodiment, the polysaccharide adsorbent is heparin.

In addition to mixed carbohydrates, it is possible to include additional binding moieties specific for the analyte. These include proteins, peptides, antibodies, affibodies, nucleic acids and other specific binding moieties (See, US Pat. Pub. 2003/0044769, incorporated by reference herein).

C. Attachment of Polysaccharide Adsorbents onto the Surface of the Adsorption Media Polysaccharides can be linked onto the surface of the adsorption media by single covalent bond end-point attachment (e.g., covalent attachment through the terminal residue of the heparin molecule). A single covalent attachment at the terminal group of the molecule to be attached, as compared to non-covalent attachment or multi-point attachment, advantageously provides better control of the orientation of the immobilized molecules while maximizing their surface density. In particular, the end-point attachment of these long chain carbohydrates provides a brush-type molecular surface architecture that leads to a higher concentration of accessible positions on the carbohydrate oligomers available for analyte/pathogen binding. In some instances, pRBCs attach to full-length heparin (e.g., heparin with a mean molecular weight of more than 10 kDa) coated surfaces much more efficiently than to conventional surfaces coated with heparin fragments, as is generally employed in the prior art.

Covalent attachment of a carbohydrate (e.g., a polysaccharide) to a solid substrate provides control of parameters such as surface density and orientation of the immobilized molecules as compared to non-covalent attachment. These parameters have been shown to provide adsorbate binding to the immobilized carbohydrate molecules. In certain embodiments, the surface concentration of the carbohydrate on the solid substrate is in the range of 0.01 to about 0.5 $\mu g/cm^2$, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19 or 0.2 $\mu g/cm^2$. In other embodiments, the surface concentration of the adsorbent(s) on the solid substrate is in the range of 0.001-2.0 $\mu g/cm^2$. In another embodiment, the surface concentration of the adsorbent(s) on the solid substrate is in the range of 0.005-0.5 $\mu g/cm^2$.

In some embodiments, the surface concentration of the adsorbent on the solid substrate is in the range of 1 $\mu g/cm^2$ to 20 $\mu g/cm^2$, e.g., 1 $\mu g/cm^2$, 2 $\mu g/cm^2$, 3 $\mu g/cm^2$, 4 $\mu g/cm^2$, 5 $\mu g/cm^2$, 6 $\mu g/cm^2$, 7 $\mu g/cm^2$, 8 $\mu g/cm^2$, 9 $\mu g/cm^2$, 10 $\mu g/cm^2$, 11 $\mu g/cm^2$, 12 $\mu g/cm^2$, 13 $\mu g/cm^2$, 14 $\mu g/cm^2$, 15 $\mu g/cm^2$, 16 $\mu g/cm^2$, 17 $\mu g/cm^2$, 18 $\mu g/cm^2$, 19 $\mu g/cm^2$, and 20 $\mu g/cm^2$. In other embodiments, the surface concentration of the adsorbent on the solid substrate is in the range of 5 $\mu g/cm^2$ to 15 $\mu g/cm^2$, e.g., 5 $\mu g/cm^2$, 6 $\mu g/cm^2$, 7 $\mu g/cm^2$, 8 $\mu g/cm^2$, 9 $\mu g/cm^2$, 10 $\mu g/cm^2$, 11 $\mu g/cm^2$, 12 $\mu g/cm^2$, 13 $\mu g/cm^2$, 14 $\mu g/cm^2$, and 15 $\mu g/cm^2$.

In some embodiments, mannose, derivatives of mannose and oligomers of mannose are reductively coupled to primary amines on aminated substrates such as aminated beads by reductive amination. Coupling of the open aldehyde form of a reducing mannose to a bead results in a stable secondary amine. Non-reducing mannoses having a reactive amine can be coupled to a bead with an intermediate having an aldehyde functionality. For instance, mannose is attached to an amine containing substrate by (a) contacting an aminated substrate with an aqueous solution containing a mannose to form a Schiff base intermediate; and (b) contacting the Schiff base with a reducing agent to attach the mannose. In some embodiments, if the mannose is a nonreducing mannose, an intermediate aldehyde (e.g., glutardialdehyde) is attached to the amine substrate prior to the non-reducing mannose.

Mannose can be dissolved in aqueous solution such as an acidic aqueous solution. The mannose aqueous solution is contacted with an aminated substrate such as an aminated bead. A Schiff's base is generated. The Schiff's base is thereafter reduced with a reducing agent. The reducing agent can be, for example, sodium cyanoborohydride or sodium borohydride. In certain instances, the solid substrate is also reacted with heparin having a reactive aldehyde functionality.

For heparin attachment, a more reactive aldehyde function in the reducing terminal residue can be achieved by partial, nitrous acid degradation. This shortens the reaction time, but the immobilized heparin will have a lower molecular weight. The coupling is performed in aqueous solution, by reductive amination (cyanoborohydride).

Covalent attachment of full-length heparin molecules to a surface can be achieved by the reaction of an aldehyde group of the heparin molecule with a primary amino group present on the surface of the adsorption media. An inherent property of all carbohydrates is that they have a hemiacetal in their reducing end. This acetal is in equilibrium with the aldehyde form and can form Schiff's bases with primary amines. These Schiff's bases may then be reduced to stable secondary amines. In some embodiments, full-length heparin is surface immobilized onto the solid substrate by covalent conjugation. In other embodiments, full-length heparin is covalently attached to said adsorption media via a stable secondary amino group.

In some embodiments, the immobilized full-length heparin molecules have a mean molecular weight of more than 10 kDa. In other embodiments, the immobilized heparin molecules have a mean molecular weight of more than 15 kDa. In another embodiment, the immobilized heparin molecules have a mean molecular weight of more than 21 kDa. In yet another embodiment, the immobilized heparin molecules have a mean molecular weight of more than 30 kDa. Preferably, the immobilized heparin molecules have a mean molecular weight within the range of 15-25 kDa. The mean molecular weight may also be higher, such as in the range of 25-35 kDa.

In certain instances, various methods of making adsorbents and the adsorbents per se are disclosed in U.S. Pat. Nos. 8,663,148 and 8,758,286; and U.S. Application Publication Nos. 2009/0136586, 2012/0305482, and US 2014/0231357, the disclosures of which are herein incorporated by reference for all purposes.

D. Analytes/Pathogens That Bind Adsorbents Bound to the Adsorption Media

The adsorbents attached to the adsorption media can be used to bind to a analyte/pathogen of interest in a sample. In some embodiments, the sample is selected from the group consisting of whole blood, serum, plasma, urine, feces, sputum, tears, saliva, bronchial lavage fluid, other bodily fluid, and combinations thereof. In some instances, the sample is whole blood from a subject, e.g., a human subject.

The analyte/pathogen can include, but is not limited to, *Plasmodium falciparum, Plasmodium vivax, Plasmodium ovale, Plasmodium malariae*, Ebola virus (EBOV), *Streptococcus aureus, Streptococcus pyogenes, Streptococcus pneumonia, Neisseria meningitides, Pseudomonas aeruginosa, Escherichia coli*, carbapenem-resistant *enterobacteriaceae* (CRE) bacteria, (e.g., carbapenem-resistant *Escherichia coli* and carbapenem-resistant *Klebsiella* pneumoniae), an ESBL-producing pathogen (e.g., ESBL-producing *E. coli*, ESBL-producing *K. pneumonia*, and ESBL-producing *K. oxytoca*), vancomycin-resistant *enterococci* (VRE) bacteria (e.g., vancomycin-resistant *E. faecalis* and vancomycin-resistant *E. faecium*), *Acinetobacter baumannii, Klebsiella pneumoniae, Klebsiella oxytoca, Enterococcus faecalis, Enterococcus faecium, Candida albicans*, cytomegalovirus (CMV), herpes simplex virus 1 (HSV1), herpes simplex virus 2 (HSV2) and any combination thereof.

In certain other instances, the analyte/pathogen of interest includes, but is not limited to, Hepatitis A Virus (HAV), Hepatitis B Virus (HBV), Hepatitis C Virus (HCV), Hepatitis D Virus (HDV), Hepatitis G Virus/GB-C Virus (HGV/GBV-C), Human Immunodeficiency Virus types 1 and 2 (HIV-1/2), Human T-cell Lymphotropic Virus types I and II (HTLV-I/II), Cytomegalovirus (CMV), Epstein-Barr Virus (EBV), TT Virus (TTV), Human Herpes virus type 6 (HHV-6), SEN Virus (SEN-V), and Human Parvovirus (HPV-B 19).

Additional viruses of interest include, but are not limited to, human herpes virus type 7 (HHV-7), human herpes virus type 8 (HHV-8), influenza type A viruses, including subtypes H1N1 and H5N1, severe acute respiratory syndrome (SARS) coronavirus, and RNA viruses that causes hemorrhagic fever, such as Arenaviridae (e.g., Lassa fever virus (LFV)), Filoviridae (e.g., Ebola virus (EBOV) and Marburg virus (MBGV)); Bunyaviridae (e.g., Rift Valley fever virus (RVFV) and Crimean-Congo hemorrhagic fever virus (CCHFV)); and Flaviviridae (West Nile virus (WNV), Dengue fever virus (DENY), yellow fever virus (YFV), and (GB virus C (GBV-C), formerly known as Hepatitis G virus (HGV)).

In certain instances, the bacteria include, but are not limited to, *Treponema Pallidum* (TP, the agent of syphilis), *Yersinia Enterocolitica*, and *Staphylococcus* and *Streptococcus* species (common agents of bacterial contamination), and parasites such as *Plasmodium* species (the agent of malaria), *Trypanosoma Cruzi* (agent of Chagas' disease), and *Babesia Microti* (agent of babesiosis). Additional bacteria include, but are not limited to, *Staphylococcus epidermidis, Bacillus cereus, Eikenella corroders, Listeria monocytogenes, Streptococcus agalactiae, Haemophilus influenzae, Neisseria meningitidis, Neisseria gonorrhoeae, Bacteroides fragilis, Bacillus anthracis, Yersinia pestis, Yersinia enterocolitica, Francisella tularensis, Brucella abortus, Serratia marcescens, Serratia liquelaciens, Pseudomonas fluorescens* and *Deinococcus radiodurans*.

In addition, emerging blood-borne pathogens such as *Candida* sp., including *Candida albicans, Aspergillus* sp., including *Aspergillus fumigatus*, Hepatitis E Virus (HEV), Human Herpes virus type 8 (HHV-8), *Borrelia Burgdorferi* (agent of Lyme disease), and the unknown agent of Creutzfeldt-Jakob disease (CJD) can be detected.

Pathogens known to bind to heparin/heparan sulfate can used in the methods described herein. Non-limiting examples of such pathogens include bacteria, e.g., *Bacillus anthracis, Bacillus cereus, Borrelia burgdorferi, Bordetella pertussis, Chlamydia pneumoniae, Chlamydia trachomatis, Haemophilus influenzae nontypable, Helicobacter pylori, Listeria monocytogenes, Mycobacterium tuberculosis, Neisseria gonorrhoaea, Neisseria meningitidis, Orientia tsutsugamushi, Porphyromonas gingivalis, Pseudomonas aeruginosa, Staphylococcus aureus, Streptcoccus agalactiae, Streptococcus pyogenes, Steptococcus pneumoniae, Yersinia enterocolitica*; viruses, e.g., adeno-associated virus type 2, adenovirus, coronavirus, coxsackievirus, cytomegalovirus, Dengue virus, FMDV, HSV1, HSV2, hepatitis B virus, hepatitis C virus, HHV8, HIV1, HPV, HTLV1, Japanese encephalitis virus, pseudorabies virus, respiratory syncytial virus, rhinovirus, sindbis virus, vaccinia virus, West Nile virus, Yellow Fever virus; parasites, e.g., *Giardia Zambia, Leishmania* spp., *Encephalitozoon* spp., *Neospora caninum, Plasmodium* spp., *Toxoplasma gondii, Trypanosona cruzi*, and prions. See, e.g., Barlett and Park, "Chapter 2 Heparan Sulfate Proteoglycans in Infection" in M. S. G. Pavao, ed. *Glycans in Diseases and Therapeutics, Biology of Extracellular Matrix*, Heidelberg: Spring-Verlag, 2011.

E. Methods for Detecting Analytes/Pathogens

Provided herein is a method for reducing blood cells in a biological sample from an individual who is infected or is suspected of being infected with said analyte/pathogen. The method can be used to remove blood cells which can interfere with the sensitivity of conventional techniques used to detected the analyte/pathogen of interest. The method can include exposing the sample that includes blood cells to the adsorption media described herein under conditions to form an adhering complex that includes the analyte/pathogen and the adsorption media. The blood cells of the sample can be separated from the adhering complex by, for example, gravity, or other means that maintain the adhering complex. In some instances, a saline solution, such as a normal saline solution, e.g., a solution of about 0.90% w/v of NaCl, about 300 mOsm/L, a 0.01N saline solution, or a similar solution, is applied to the adhering complex including adsorption media to wash the remaining blood cells away.

Also provided herein is a method for concentrating analytes/infectious pathogens in a sample obtained from an individual who is infected or is suspected of being infected with said analytes/pathogens. The sample can be exposed to the adsorption media described herein under conditions to form an adhering complex that includes the adsorption media and the analytes/pathogens. Components of the sample that are not part of the adhering complex can be separated by, for example, gravity, without disturbing the adhering complex. The adhering complex including the adsorption media can be washed with a wash buffer such as a normal saline solution or a solution that maintains (preserves) the complex. In some instances, a normal saline solution is a solution of about 0.90% w/v of NaCl, about 300 mOsm/L, a 0.01N saline solution, or a similar solution. The complex can be disrupted to separate the analytes/pathogens from the adsorption media by applying an elution buffer, such as a high ionic saline solution, to the complex. In some instances, a high ionic saline solution is a 2N saline solution. In other cases, the elution buffer is a buffer that can disrupt the binding of the polysaccharide adsorbent and the analyte/pathogen. In some embodiments, different analytes/pathogens can be eluted from the adsorption media in different fractions by using various elution buffers selected for the particular analyte/pathogen of interest. Similar to a chromatography column, specific analytes/pathogens can be eluted at different time in different pools. The analyte/pathogen of interest can be eluted in one or more fractions.

This process concentrates analytes/pathogens, which can then be identified and analyzed using standard methods known to those in the art. For example, bacterial, viral, fungal, protozoan, parasitic, and microbial pathogens can be detected using assays, such as, colorimetric assays, immunoassays (e.g., sandwich assays or dipstick assay), enzyme-linked immunosorbent assays (ELISAs), PCR-based assays (e.g., RT-PCR, qPCR, TaqMan® assays), pathogen growth assays (e.g., drug resistance or antibiotic resistance assays), and variants thereof. For instances, HCV RNA is detected using RT-PCR using a standard kit, such as COBAS® AmpliPrep/COBAS® TaqMan® HCV test (Roche Diagnostics, Indianapolis, Ind.) and RealTime HCV Genotype II (Abbott Molecular, Abbott Park, Ill.). Ebola virus can be detected using, for example, BioFire Diagnostics' FilmArray and the CDC's Ebola Virus VP40 Real-time RT-PCR Assay.

Drug-resistant pathogens can be detected by culturing the pathogen in the presence of the drug. For example, a pathogen suspected to be a carbapenem-resistant *Klebsiella* or *E. coli* can be used to inoculate a growth media containing ertapenem or meropenem. After propering culturing, the incubated broth culture can be subculture onto a MacConkey agar plate. The following day, the agar plate can be examined for lactose-fermenting (pink-red) colonies. In addition, the isolated colonies can be screened using a phenotypic test for carbapenemase production, such as the Modified Hodge Test (MHT).

In certain instances, the analyte of interest can be detected and/or identified using typical laboratory techniques such as enzyme-linked immunosorbent assay (ELISA), radioimmunoassay (MA), and affinity chromatography. For example, in certain instances a commercial available ELISA kit can be used, or is easily developed. In the ELISA, a specific antibody is passively absorbed to a plate. The nonspecific sites are blocked with a protein solution which has no active part in the specific immunochemical reaction of a particular assay. A specific analyte/pathogen is captured by the antibody on the surface and then detected by another antibody with an enzyme label. The enzyme label is reacted with specific reagents and the presence of the analyte is detected and identified.

In certain other instances, a quartz crystal microbalance (QCM) can be used to detect the analyte adsorbed to the surface. A quartz crystal microbalance is a very sensitive and inexpensive detector/sensor that produces a frequency shift in quartz crystal vibration when molecules interact with its surface. The QCM detects a physical change such as a mass per unit area by measuring the change in frequency of a quartz crystal resonator. In liquid, the QCM is highly effective at determining the affinity of molecules to surfaces functionalized with recognition sites. Larger entities such as viruses and microbes can also be recognized. For example, QCMs can be coupled to antibodies, allowing for the selective sensing of an antibody conjugate. In certain instances, the eluent contains an analyte or pathogen of interest. The QCM has conjugated thereto an antibody specific for the analyte. By contacting the QCM with eluent containing the analyte/pathogen, the analyte binds to the surface of the QCM, and the QCM senses the binding, presence and its identity. Other affinity molecules can also be bound to the surface such as nucleic acids, carbohydrates, peptides, proteins and the like.

In still other instances, surface plasmon resonance (SPR) techniques can be used to detect the presence and or identity of the analyte/pathogen. Surface plasmon is a quantum name for an electric charge density wave that propagates on an interface between a metal and a dielectric, just like photon is a quantum name for a light wave. Surface plasmons resonate upon excitation by electromagnetic radiation entering an interface of metallic material and a dielectric material. The surface plasmon responds to changes in the environment in close proximity to the interface. This fact makes surface plasmon resonance useful for the detection of biomolecular interactions. Like QCM, it is possible to label the SPR surface with either an antibody or binding moiety such as an antigen of an analyte/pathogen of interest.

The method for concentrating analytes/pathogens from blood, e.g., whole blood or serum, or for reducing blood cells from blood can include contacting the blood with a solid, essentially non micro-porous substrate which has been surface treated with a polysaccharide adsorbent that has a binding affinity for the analytes/pathogens to be removed (the adsorbates). The size of the interstitial channels within said media is balanced with the amount of media surface area and the surface concentration of binding sites on the media in order to provide adequate adsorptive capacity while also allowing relatively high flow rates of blood through the adsorbent media. The result is that transport of adsorbates to the binding sites on the media occurs largely by forced convection, not by slow diffusion. By (forced) convection is meant, for example, flow produced by a pressure gradient generated by a pump, or a syringe by the application of external pressure to a flexible container (or internal pressure to a rigid container), by a gravity head/elevation difference, or by the difference in arterial pressure and venous pressure in the patient being treated with an extracorporeal device.

F. Method of Diagnosing a Malaria Infection

Provided herein are methods of using an adsorption media comprising a heparin-immobilized solid substrate to determine the presence of a malaria infection. A sample taken from an individual suspected of having malaria can be tested for infected red blood cells (RBCs) or parasitized RBCs using the method described herein. This method is based on the observation that heparan sulfate binding proteins located on the cell surface of parasitized RBCs can adhere to heparin, heparan sulfate or other polysaccharides that are bound on a solid surface. In addition, the method can be utilized to determine whether the individual should be administered an anti-malaria therapy. Furthermore, the method can be used to monitor the progression of malaria in an individual receiving said therapy.

A sample can be obtained from a subject (e.g., human individual) suspected of having a malaria infection. In some embodiments, the sample is a member selected from the group consisting of whole blood, serum, plasma, urine, sputum, bronchial lavage fluid, tears, nipple aspirate, lymph, saliva, cerebral spinal fluid, tissue and combinations thereof. Preferably, the sample is whole blood.

The sample is then contacted with the adsorption media under conditions to allow the polysaccharide adsorbent on the surface of the solid substrate to bind to a parasitized red blood cell if present in the sample, to form an adhering complex.

In some instances, after the formation of the adhering complex the sample and the adsorption media are separated without disrupting or separating the complex from the media.

The presence of the adhering complex is detected by inspecting the color of the adsorption media within the visible light spectrum. (e.g., wavelength of about 400 nm to about 700 nm). In some instances, the detectable color is within the wavelength range of about 625 nm to 740 nm, or range corresponding to the color red or variations thereof. The color of the adsorption media can be determined by using an optical detector of visible light or the human eye.

In certain instances, it is possible to concentrate the analyte (e.g., virus, pathogen, bacteria, cytokine or adhering complex) on the media and detect the analyte by a color change of the media. In an alternative embodiment, it is possible to concentrate the analyte to be detected by eluting the analyte from the column, concentrating the analyte and measuring a color change of media. Other forms of detection are also possible.

In some embodiments, the color of the test adsorption media is compared to a control adsorption media. In some embodiments, the control media (e.g., negative control for infection) is an adsorption media that has been exposed to a sample taken from a healthy control such as a subject who does not have a malaria infection. In other embodiments, the control media (e.g., positive control) is an adsorption media that has been exposed to a sample taken from a subject having a malaria infection (e.g., uncomplicated or severe malaria infection).

If the adsorption media from the test subject has a similar color to that of the healthy control, then the assay indicates the absence of the adhering complex. Yet, if the adsorption media from the test subject has a similar color to that of the positive control, then the assay indicates the presence of the adhering complex, and thus a malaria infection.

If the presence of the adhering complex is detected, then the subject can be administered an anti-malaria therapy. Non-limiting examples of an anti-malaria therapy include chloroquine (Aralen), quinine sulfate (Qualaquin), hydroxychloroquine (Plaquenil), atovaquone-proguanil (Malarone), artemether-lumefantrine (Coartem), mefloquine (Lariam), primaquine, amodiaquine, quinine, quinidine, doxycycline, clindamycin, sulfonamides, such as sulfadoxine and sulfamethoxypyridazine, pyrimethamine, halofantrine, artemisinin, artemisinin derivatives thereof, and combinations thereof. Artemisinin derivatives include artemether, artesunate, dihydroartemisinin, artenimol, artemotil, and arteether. Other artemisinin derivatives that are suitable anti-malaria drugs are found in, for example, U.S. Pat. Nos. 8,722,910; 8,481,757; 8,304,440; 7,851,512; 7,776,911; 7,084,132; 6,586,464; 6,362,219; and 6,306,896; and U.S. Patent Appl. Pub. Nos. 2012/0258945, 2013/0072513, 2013/071474, 2014/011829, 2014/011830, and 2014/256761.

G. Infected RBCs can Attach to RBC Binding Molecules on the Surface of the Adsorption Media Infected red blood cells can be retained on the surface of an absorption media bound by a polysaccharide such as but not limited to, heparan sulfate, heparin, condroitin sulfate, and derivatives thereof. Non-limiting examples of infecting agents, such as viruses and pathogens (e.g., bacteria and parasites) that can bind to heparan sulfate, heparin and analogs thereof include bacteria, e.g., *Bacillus anthracis, Bacillus cereus, Borrelia burdorferi, Bordetella pertusis, Chlamydia pneumoniae, Chlamydia trachomatis, Hemophilus influenzae, Helicobacter pylori, Listeria monocytogenes, Mycobacterium tuberculosis, Neisseria gonorrhoaea, Neisseria meningitidis, Orientia* tsutsugamushi, *Porphyromonas gingivalis, Pseudomonas aeruginosa, Staphylococcus aureus, Streptococcus agalactiae, Streptococcus pyogenes, Streptococcus pneumoniae*, and *Yersinia enterocolitica*, vaccinia viruses, e.g., cowpox virus, rabbitpox virus, myxoma virus, and Shope fibroma virus, HIV-1, HPV, HTLV1, hepatitis C virus, hepatitis B virus, adeno-associated viruses (AAV), adenoviruses, coronaviruses, coxsackieviruses, cytomegaloviruses, herpesviruses, e.g., Murid Herpesvirus-4 (MuHv-4), Kaposi's sarcoma-associated herpesvirus (KSHV), Ebstein-Barr virus (EBV), FMDV, herpes simplex viruses, e.g., HSV-1 and HSV-2, pseudorabies virus (PrV), pseudorabies virus, respiratory syncytial virus, rhinoviruses, sidbis viruses, flaviviruses, e.g., dengue viruses (dengue 1, 3, 4), japanese encephalitis virus, kunjin virus, Murray Valley encephalitis virus, powassan virus, St. Louis encephalitis virus, tick-borne encephalitis virus, West Nile virus, yellow fever virus, pestiviruses, e.g., viruses that cause border disease, bovine viral diarrhea, classical swine fever, hemorrhagic fever viruses, e.g., Ebola virus, Marburg virus, Lassa fever virus, Rift Valley virus, other arenaviridaie viruses, other bunyaviridae viruses and other filoviridae viruses, and parasites, e.g., *Giardia lamblia, Leishmania* ssp., *Encephalitozoon* spp., *Neospora caninum, Plasmodium* ssp., *Toxoplasma gondii*, and *Trypanosoma cruzi*.

In certain aspects, the method for detecting an infectious pathogen present in a biological sample obtained from a subject who is suspected of being infected, includes: (a) contacting the biological sample obtained from the subject with an adsorption media under conditions to form an adhering complex comprising the adsorption media and the pathogen; (b) separating the adhering complex from components of the biological sample that are not included in the complex while maintaining the complex; and (c) collecting the pathogen of the adhering complex, wherein the pathogen or a component of the pathogen is collected after using an enzymatic digestion while the pathogen is resident on the adsorption media.

In some embodiments, the digestion is with one or more enzymes such as a protease or DNase while the pathogen (e.g. virus) is still adsorbed to the media.

H. Concentrators and Kits

In certain embodiments, the present invention provides a concentrator in a form that resembles a hypodermic syringe. The FIGURE herein is one embodiment of the concentrator of the present invention. The concentrator 100 has a barrel 118 filled with adsorption media 105. In certain instances, the barrel is a hollow cylindrical barrel portion 118 with adsorbate contained therein 105, with one end terminating in an outlet tube 117 of a diameter smaller than the diameter of the cylindrical barrel portion 118. In some instances, a hollow hypodermic needle 112 communicates with the outlet tube 117 of the barrel portion 118. In some instances, one or more different polysaccharide adsorbents, e.g., 1, 2, 3, 4, 5 or more different polysaccharide adsorbents, are attached to the adsorption media. The concentrator 100 has a plunger 130 with a shaft 115 that allows the user to remove a sample from a subject using a needle 112 which is attached to the concentrator 100. The needle can be of various gauges as are typical for the sample being removed from a subject. In certain aspects, the concentrator 100 has an optional reservoir 110 filled with fluid such as saline, water or a buffer. In operation, the needle is inserted into a subject to remove a sample such as blood. As the plunger 130 is withdrawn from the barrel 118 using shaft 115, a breakable barrier 108 between the reservoir 110 and media 105 is broken by action of the withdrawn plunger, allowing the fluid to be drawn through the media to wet or prime the media. The fluid (e.g., saline) is drawn through the media 105 and ends in area 121. In certain instances, the optional reservoir 110 comprises a breakable seal or barrier 108 such as foil, an adhesive, or plastic, disposed between the outlet tube and adsorbate 105.

As a sample (e.g., blood) is drawn through the media, the analyte or pathogen contained therein adheres to the media. In certain instances, the withdrawn plunger 115 can be pushed by the user back toward the barrel of the concentrator. In certain instances, the sample such as the removed blood can be injected back and returned to the subject. This back and forth operation of the plunger can be repeated several times in order to concentrate the analyte/pathogen onto the media. The operation of removing the plunger back and forth can be repeated 1, 2, 3, 4, 5, 6 or even more times.

The analyte/pathogen can be removed from the media using the methods taught herein. For example, in certain instances, normal saline can be used to remove any adhering cells and debris. Thereafter, 2N saline can be used to remove the analyte or pathogen. In certain other instances, a buffer or saline is used to remove all adhering sample components.

In still other aspects, a sterilizing filter is used which can be attached to the outside of the concentrator 100. For example, the needle can be removed and the filter is attached, or the needle has a filter adapter. The filter allows the concentrator to be adaptable for field use. For example, in the field, sterile water or fluid may not be available. In certain instances, impure water or fluid is drawn through the filter and, now sterilized through the media 105. In certain instances, reservoir 110 is optionally removed and the sterilized water or sterilized fluid drawn through the sterilizing filter primes or wets the media.

In one embodiment, the present invention provides a kit which comprises a concentrator. In certain aspects, the kit includes a package that can be used to hold the concentrator before and after use. The concentrator can be used as discussed above and thereafter sent out for further analysis. The kit optionally includes instructions for use.

In one aspect, the concentrator comprises:

a) a hollow cylindrical barrel portion 118 with adsorbate contained therein 105, one end terminating in an outlet tube 117 of a diameter smaller than the diameter of the cylindrical barrel portion 118;

b) a hollow hypodermic needle 112 communicating with the outlet tube 117 of said barrel portion 118;

c) a plunger 130 comprising an elastomeric material disposed within and adapted for reciprocal movement within said cylindrical barrel 118;

d) shaft means 115 attached to said plunger 130 and extending outwardly of the end of said barrel portion 118 opposite the outlet tube 117 and operative to impart reciprocating movement to said plunger 130 toward and away from the outlet tube of said barrel portion 118; and f) an optional rerservoir 110 with a breakable seal 108, disposed between the outlet tube and adsorbate.

III. Examples

The following examples are offered to illustrate, but not to limit, the claimed invention.

Example 1: Diagnosing Malaria in Individuals Using a Heparin Conjugated Adsorption Media This example illustrates the use of a heparin conjugated adsorption media to detect parasitized red blood cells (pRBCs) in a blood sample from an individual suspected of having a malaria infection.

A whole blood sample is taken from an individual by standard methods and following clinical guidelines. The blood sample (test sample) is contacted with heparin immobilized on the surface of the adsorption media under conditions to allow any parasitized red blood cells in the test sample to attach to the immobilized heparin. Next, the unbound sample is removed without disturbing the adhering complex formed by the pRBCs and the heparin on the test adsorption media. The test media is then observed using the naked eye to detect any change in color compared to an adsorption media to whole blood free of parasitized red blood cells. If a color change is detected (e.g., the test media appears more red), this indicates that the individual is likely to have a malaria infection.

The color of the test media is compared to the color of an adsorption media exposed to a blood sample from a healthy control, such as an individual that does not have a malaria infection. The individual is diagnosed as not having a malaria infection if the test adsorption media and the healthy control media have a similar color. The color of the test media is compared to the color of an adsorption media exposed to a blood sample from a positive control, such as a patient with uncomplicated malaria or severe malaria. The individual is diagnosed as having a malaria infection if the test adsorption media and the positive control media have a similar color.

Example 2: A System for Diagnosing a Viral Infection and Extracorporeally Treating the Infection This example illustrates a system of the present invention.

The system comprises at least two cartridges, wherein the first cartridge is a smaller diagnosis cartridge and the second cartridge is a larger therapeutic cartridge. The first or diagnostic cartridge contains a short column between 3-6 ml, which is filled with heparinized beads. The first cartridge is used for the detection of a blood sample suspected of containing hepatitis C virus (HCV).

A 2 ml blood sample is obtained from the subject. The blood sample is loaded onto the diagnosis column and forms an adhering complex comprising the adsorption media and HCV. Thereafter, the column is washed and with a 0.01 N saline wash buffer. The column is thereafter washed by applying a 2N saline elution buffer to the concentrate the infectious pathogen.

HCV RNA is detected using RT-PCR using a standard kit, such as COBAS® AmpliPrep/COBAS® TaqMan® HCV test (Roche Diagnostics, Indianapolis, Ind.) and RealTime HCV Genotype II (Abbott Molecular, Abbott Park, Ill.).

The second larger therapeutic cartridge is built with heparinized coated beads. A 300 ml adsorption column is fixed to a vertical stand. The 300 ml of beads are then added to the cartridge and sealed.

The patient uses extracorporeal removal of the HCV using the therapeutic column. Binding of hepatitis C virus to the heparin occurs. The heparin is effective to identify and remove the infectious agent.

Example 3: Processing a Sample from an Individual Suspected of being Infected with Ebola Virus Prior to Detecting the Virus This example illustrates the use of an exemplary embodiment of the present invention for isolating Ebola virus particles from a biological sample from a subject infected with Ebola virus.

An Ebola infected whole blood sample is circulated over a column filled with heparinized beads. At various time points, the flow-through from the column is collected and tested for the presence of Ebola. The heparinized beads are gently washed with a 0.01N saline solution without disturbing the bead matrix. The flow-through from the washing step is collected and tested for Ebola. The flow-through contains cells such as blood cells that can interfere with the sensitivity of commercial viral detection assays. An elution buffer containing 2N saline solution is applied to the column and the eluent is collected. The eluent is tested for the presence of Ebola using the CDC's protocol "Ebola Virus VP40 Real-Time RT-PCR assay. This method uses a TaqMan® assay to detect the viral protein 40 of the Ebola virus.

Example 4: Processing and Concentrating Pathogens from a Blood Sample Using Polysaccharide Adsorbent Modified Beads This example illustrates the use of an exemplary embodiment of the present invention for removing and concentrating 14 different pathogens from a biological sample.

Approximately 0.6 grams of adsorption media, such as either heparin media alone, mannose media alone, polyethylenimine PEI media, a composite of heparin and mannose media, or a composite of heparin and mannose media and naked beads was packed into 2.5 ml filter syringes (Mobicol) with 100 µm endplates. 2 ml of the pathogen suspensions in blood was prepared by culturing the pathogens (e.g., *P. aeruginosa*, MRSA, ESBL-producing *K. pneumonia*, carbapenem-resistant *K. pneumonia*, *K. pneumonia*, carbapenem-resistant *E. coli*, *E. coli*, *S. pneumonia*, *E. faecalis*, vancomycin-resistant *E. faecalis*, *E. faecium*, *A. baumannii*, *C. albicans*, and CMV) overnight and diluting to the appropriate concentrations (Table 1). The packed filter syringes were rinsed with 3 ml of PBS, followed by passing the pathogen suspension over the syringes three times. 1.0 ml of the elution buffer (2N saline solution) was passed over the syringes and the flow-through (eluent) was collected. Standard dilution and plating techniques were used to enumerate the pathogens of the eluent. The test was replicated either two times or three times for each media and pathogen combination that was analyzed. The results are shown in Tables 1 and 2.

TABLE 1

Concentration of Pathogen After Passage Over Modified Adsorption Media
Pathogen Count (CFU/ml or PFU/ml)

| Bacteria | Starting Concentration | Ending Concentration | | | | |
|---|---|---|---|---|---|---|
| | | Heparin | Mannose | PEI | Hep/Man (0.6 g) | Hep/Man/PEI (0.6 g) |
| *P. aeruginosa* | 4.02E+05 | 5.27E+05 | 3.79E+05 | 4.73E+05 | 4.67E+05 | 2.75E+05 |
| MRSA | 1.21E+05 | 1.02E+04 | 1.22E+05 | 1.48E+04 | 2.03E+04 | 3.07E+03 |
| *K. pneumoniae* (ESBL) | 2.82E+05 | 1.72E+05 | 1.98E+05 | 1.80E+05 | | |
| *K. pneumoniae* (CRE) | 1.40E+05 | 7.83E+01 | 1.70E+02 | 2.07E+02 | 2.07E+02 | 1.88E+02 |
| *K. pneumoniae* | 4.02E+05 | 2.55E+05 | 2.66E+05 | 1.64E+05 | | |
| *E. coli* (CRE) | 2.57E+05 | 1.90E+02 | 2.25E+02 | 1.83E+02 | 2.00E+02 | 2.27E+02 |
| *E. coli* | 6.15E+05 | 1.54E+03 | 8.92E+02 | 1.01E+03 | | |
| *S. pneumoniae* | 9.80E+04 | 4.60E+04 | 5.80E+04 | 7.48E+04 | | |
| *E. faecalis* | 6.43E+05 | 6.17E+03 | 5.83E+03 | 3.34E+03 | | |
| *E. faecalis*(VRE) | 6.17E+05 | 5.40E+04 | 5.42E+04 | 4.80E+04 | | |
| *E. faecium* | 9.17E+05 | 4.00E+05 | 5.67E+05 | 5.33E+05 | | |
| *A. baumannii* | 1.83E+05 | 3.82E+04 | 1.82E+04 | 8.50E+04 | | |
| *C. albicans* | 3.35E+05 | 2.15E+05 | | | | |
| CMV | 7.59E+04 | 1.35E+04 | | | | |

TABLE 2

Amount of Pathogen Removed From a Blood Sample
CFU or PFU removed per gram of media

| | Heparin | Mannose | PEI | Hep/Man | Hep/Man/PEI |
|---|---|---|---|---|---|
| *P. aeruginosa* | 0.00E+00 | 7.67E+04 | 0.00E+00 | 0.00E+00 | 4.23E+05 |
| MRSA | 3.69E+05 | −3.33E+03 | 3.54E+05 | 3.36E+05 | 3.93E+05 |
| *K. pneumoniae* (ESBL) | 3.67E+05 | 2.80E+05 | 3.40E+05 | | |
| *K. pneumoniae* (CRE) | 4.66E+05 | 4.66E+05 | 4.66E+05 | 4.66E+05 | 4.66E+05 |
| *K. pneumoniae* | 4.90E+05 | 4.53E+05 | 7.93E+05 | | |
| *E. coli* (CRE) | 8.56E+05 | 8.56E+05 | 8.56E+05 | 8.56E+05 | 8.56E+05 |
| *E. coli* | 2.04E+06 | 2.05E+06 | 2.05E+06 | | |
| *S. pneumoniae* | 1.73E+05 | 1.33E+05 | 7.73E+04 | | |
| *E. faecalis* | 2.12E+06 | 2.12E+06 | 2.13E+06 | | |
| *E. faecalis* (VRE) | 1.88E+06 | 1.88E+06 | 1.90E+06 | | |
| *E. faecium* | 1.72E+06 | 1.17E+06 | 1.28E+06 | | |

TABLE 2-continued

Amount of Pathogen Removed From a Blood Sample
CFU or PFU removed per gram of media

|  | Heparin | Mannose | PEI | Hep/Man | Hep/Man/PEI |
|---|---|---|---|---|---|
| A. baumannii | 4.83E+05 | 5.49E+05 | 3.27E+05 |  |  |
| C. albicons | 4.00E+05 | 1.12E+06 |  |  |  |
| CMV | 2.08E+05 |  |  |  |  |

The tables above illustrate the removal and concentration of 14 different pathogens using methods disclosed herein. For example, as is shown in Table 1, a MRSA sample has a starting concentration of $1.21 \times 10^5$ CFU/ml. Table 1 shows various efficiencies of the adsorbates of the present invention. After a pass or repeated passes over a column having heparin, mannose, naked bead (PEI), a mixture of heparin/mannose, or heparin/mannose and PEI, the ending concentrations of each sample was measured, recorded and tabulated.

The samples were repeatedly passed over the columns in an iterative fashion. The samples can be passed multiple times each time reducing bacteria concentrations in the sample and concentrating the bacteria or pathogen on the media.

A significant amount of pathogen is separated from the sample using the adsorption media. Table 2 is a summary table reporting the removal of pathogens using various media. After the pathogen is concentrated on the media column, it can be freed from the column and the its presence and identity can be determined. The pathogen can be concentrated by applying a volume of elution buffer that is less than the starting sample volume. Furthermore, the method can be used to remove cells and debris from the blood sample that can interfere with standard pathogen detection methods, such as colorimetric assays, immunoassays, ELISAs, PCR-based assays, and the like.

Example 5: Identification of a Pathogen Such as a Virus in a Biological Sample Using Polysaccharide Adsorbent Modified Beads This example illustrates the use of an exemplary embodiment of the present invention for removing a pathogen such as a virus (e.g., hepatitis C virus (HCV)) from a biological sample.

In this example, a digestion step is employed with one or more enzymes such as a protease or DNase while the pathogen (e.g. virus) is still adsorbed to the media. In this manner, the digestion step is performed with a much smaller volume of buffer solution i.e., much smaller than required compared to solutions needed for elution. The protease can be for example, chymotrypsin or trypsin; the DNase can be an exo or endonuclease or a restriction enzyme.

In this example, a pathogen such as a virus is concentrated on the adsorbent beads. The virus is digested with one or more enzymes while adsorbed directly on the beads. The beads are removed and PCR is performed. The steps are as follows:

1) Infected whole blood, serum, plasma, or other biological fluid is passed over heparinized beads (or other affinity ligand);
2) The biological fluid can be exposed to the heparinized beads either by passage through a small device containing the beads (e.g., the FIGURE herein), or alternatively, the adsorbent beads are added to a vessel containing a biological fluid (e.g. a well in a multi-plate reader, conical vial, test tube, etc.);
3) The virus binds to heparin (or other carbohydrate or affinity ligand);
4) The whole blood, serum, plasma, or other biological fluid is then removed from the beads by rinsing with normal saline;
   a. For a small device containing the beads, saline is passed over the beads using flow.
   b. For beads floating in a biological fluid, the beads can be separated or filtered and added to a secondary container for washing.
5) The beads with bound pathogens are then exposed to enzyme(s) for digestion;
6) The beads are removed and a PCR amplification step is performed for analysis.

It is also possible to apply this approach to a test strip with a textured heparinized (or other ligand) on the surface of the test strip.

Pathogens such as bacterial, viral, fungal, protozoan, parasitic, and microbial pathogens can be detected using assays, such as, colorimetric assays, immunoassays (e.g., sandwich assays or dipstick assay), enzyme-linked immunosorbent assays (ELISAs), PCR-based assays (e.g., RT-PCR, qPCR, TaqMan® assays), pathogen growth assays (e.g., drug resistance or antibiotic resistance assays), and variants thereof.

HCV RNA is detected using RT-PCR using a standard kit, such as COBAS® AmpliPrep/COBAS® TaqMan® HCV test (Roche Diagnostics, Indianapolis, Ind.) and RealTime HCV Genotype II (Abbott Molecular, Abbott Park, Ill.).

Example 6: Detecting *Borrelia burgdorferi* Infections in Individuals Using a Heparin Conjugated Adsorption Media This example illustrates the use of a heparin conjugated adsorption media to detect *Borrelia burgdorferi* in a blood sample from an individual suspected of having Lyme disease.

A 42-year-old male patient presents to his primary care physician complaining of a 2-week history of intermittent fever, recurring headaches, lethargy, mild joint pain and a gradually expanding rash on the back of his knee. The patient describes the headaches as increasing in severity and frequency. He recalls removing multiple ticks from his clothing after returning from a hike in the woods near his home one week prior to onset of the symptoms, but does not recall being bitten by a tick. The patient denies any photophobia, neck stiffness, vomiting, chest pain or shortness of breath. On examination, he is febrile with a temperature of 102.1° F. Physical examination is unremarkable except for a non-pruriitic, erythematous rash behind his right knee that is slightly warm. A Lyme antibody serology is negative and the patient is referred to an Emergency Department for further evaluation.

At the Emergency Department, a blood sample is taken from the patient by standard methods and following clinical guidelines. The blood sample is contacted with heparinized beads immobilized on the surface of a test adsorption media under conditions to allow any bacteria in the blood sample to attach to the immobilized heparinized beads. The blood sample is removed from the test adsorption media without disturbing the adhering complex formed by bacteria in the blood and the heparin on the test adsorption media. The heparinized beads are gently washed with a 0.01N saline solution without disturbing the bead matrix. The flow-through from the washing step is collected and tested for presence of *Borrelia burgdorferi* and *Borrelia mayonii* bacteria. The flow-through contains cells such as blood cells that can interfere with the sensitivity of commercial bacterial detection assays. An elution buffer containing 2N saline solution is applied to the test adsorption media and the eluent is collected. The eluent is tested for presence of *Borrelia burgdorferi* and *Borrelia mayonii* bacteria using a rapid PCR assay. Presence of *Borrelia burgdorferi* in the blood sample is detected. The patient is diagnosed as having a bacterial infection caused by the bacteria, *Borrelia burgdorferi*.

Example 7: Extracorporeally Treating Bacterial Infections of Genus *Borrelia* in Individuals Having Lyme Disease This example illustrates a method for extracorporeally removing an infection caused by a bacteria of genus *Borrelia* from a subject to treat Lyme disease and Jarisch-Herxheimer reaction, which takes place when antibiotics used to treat an infection kill the spirochetes, releasing toxic cellular byproducts. The Jarisch-Herxheimer is known to take place when treating spirochete infections such as syphilis, borreliosis, leptospirosis, and Q fever with antibiotics.

A 62-year-old female patient presents to the Emergency Department with evidence of systemic shock-like symptoms including hypotension, high fevers, chills and tachycardia. The patient's medical history reveals a recent diagnosis of Lyme disease and administration of intravenous antibiotics including ceftriaxone and doxycycline almost 10 hours prior. On examination, she is febrile with a temperature of 102.4° F. Physical examination ascertains two large erythematous patches on her lower abdomen. The patient recalls feeling well until several hours after the antibiotic treatment. A septic screen to diagnose possible bacterial sepsis is inconclusive. The attending physician suspects manifestation of a Jarisch-Herxheimer reaction resulting from treatment of the Lyme disease with antibiotics.

To detect presence of *Borrelia* bacteria in the blood, a 2 ml blood sample is obtained from the patient. The blood sample is loaded onto a diagnosis column of between 3-6 ml filled with heparinized beads forming an adhering complex comprising the adsorption media and *Borrelia burgdorferi*. The heparinized beads are gently washed with a 0.01N saline solution without disturbing the bead matrix. The flow-through from the washing step is collected and tested for *Borrelia* bacteria. The flow-through contains cells such as blood cells that can interfere with the sensitivity of commercial bacterial detection assays. An elution buffer containing 2N saline solution is applied to the column and the eluent is collected. The eluent is tested for the presence of *Borrelia* bacteria using a rapid PCR assay. Presence of *Borrelia burgdorferi* in the blood sample is confirmed and the patient is admitted to the hospital for treatment.

At the hospital, blood is obtained from the patient via a catheter and is transfused into a therapeutic cartridge built with heparinized coated beads. The therapeutic cartridge comprises a sealed 300 ml adsorption column filled with heparinized coated beads and is fixed to a vertical stand. The blood is transfused over the adsorption column multiple times in an iterative fashion. Each time the blood is passed over the column, *Borrelia burgdorferi* and toxic byproducts caused by antibiotics in the blood adhere to the adsorption media and concentration of *Borrelia burgdorferi* and toxic byproducts in the blood are reduced. The blood is returned to the patient. The heparin is effective to identify and treat the *Borrelia* infection and Jarisch-Herxheimer reaction in individuals having Lyme disease.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An in vitro method for removing a bacteria of genus *Borrelia* from a subject, the method comprising:
   (a) contacting a blood sample obtained from said subject with an adsorption media under conditions to form an adhering complex comprising the adsorption media and a cell present in the blood sample which is infected with the bacteria; and
   (b) removing the adhering complex from the blood sample, to thereby remove the bacteria of genus *Borrelia* and treat Lyme disease.

2. The method of claim 1, wherein the bacteria is selected from a group consisting of: *Borrelia burgdorferi*, *Borrelia mayonii*, *Borrelia afzelii*, *Borrelia garinii*, and any combination thereof.

3. The method of claim 1, wherein the adhering complex further comprises a cellular byproduct of the bacteria responsible for causing an immune response syndrome associated with Jarisch-Herxheimer reaction in the subject.

4. The method of claim 1, wherein the adsorption media is a solid substrate of high surface area having at least one polysaccharide adsorbent on the surface thereof.

5. The method of claim 4, wherein the at least one polysaccharide adsorbent is attached to the surface of the solid substrate by end-point attachment.

6. The method of claim 4, wherein said solid substrate comprises a plurality of rigid polymer beads.

7. The method of claim 6, wherein said plurality of rigid polymer beads are rigid polyethylene beads.

8. The method of claim 7, wherein the at least one polysaccharide adsorbent is a member selected from the group consisting of heparin, heparan sulfate, mannose, dextran sulfate, hyaluronic acid, salicylic acid, chitosan, polyethylenimine (PEI) and a combination thereof.

9. The method of claim 8, wherein the at least one polysaccharide adsorbent is heparin.

10. The method of claim 9, wherein the at least one polysaccharide adsorbent further comprises chitosan, PEI or a combination.

11. The method of claim 1, wherein prior to step (a), a blood sample is taken from the subject to determine the presence *Borrelia burgdorferi* using heparinized beads.

* * * * *